(12) United States Patent
Ross et al.

(10) Patent No.: US 8,384,551 B2
(45) Date of Patent: Feb. 26, 2013

(54) SENSOR DEVICE AND METHOD FOR MONITORING PHYSICAL STRESSES PLACED ON A USER

(75) Inventors: Janice Marie Ross, Mansfield, TX (US);
Johnny Ross, Jr., Mansfield, TX (US);
Jagdeepinder Singh Sanghera, Midlothian, TX (US)

(73) Assignee: Medhab, LLC, Mansfield, TX (US)

(*) Notice: Subject to any disclaimer, the term of this patent is extended or adjusted under 35 U.S.C. 154(b) by 211 days.

(21) Appl. No.: 13/070,649

(22) Filed: Mar. 24, 2011

(65) Prior Publication Data
US 2011/0214501 A1  Sep. 8, 2011

Related U.S. Application Data

(63) Continuation-in-part of application No. 12/128,498, filed on May 28, 2008, now Pat. No. 7,969,315.

(51) Int. Cl.
*G08B 23/00* (2006.01)

(52) U.S. Cl. .......... 340/573.7; 340/573.1; 340/665; 340/669; 600/592; 600/595; 600/587

(58) Field of Classification Search .......... 340/573.1, 340/573.7, 665, 666, 668, 669; 600/592, 600/595, 587
See application file for complete search history.

(56) References Cited

U.S. PATENT DOCUMENTS

| | | | |
|---|---|---|---|
| 5,042,504 A | 8/1991 | Huberti | |
| 5,107,854 A | 4/1992 | Knotts et al. | |
| 5,269,081 A | 12/1993 | Gray | |
| 5,323,650 A | 6/1994 | Fullen et al. | |
| 5,357,696 A | 10/1994 | Gray | |
| 5,373,651 A | 12/1994 | Wood | |
| 5,408,873 A | 4/1995 | Schmidt et al. | |
| 5,429,140 A | 7/1995 | Burdea et al. | |
| 5,452,269 A | 9/1995 | Cherdak | |
| 5,619,186 A * | 4/1997 | Schmidt et al. | 340/573.1 |
| 5,661,916 A | 9/1997 | Huang | |
| 5,724,265 A | 3/1998 | Hutchings | |
| 5,815,954 A | 10/1998 | Huang | |
| 5,875,571 A | 3/1999 | Huang | |
| 5,905,209 A | 5/1999 | Oreper | |

(Continued)

FOREIGN PATENT DOCUMENTS

| JP | 2005224548 | 8/2005 |
|---|---|---|
| JP | 2010507398 | 3/2010 |

(Continued)

OTHER PUBLICATIONS

Author: Jan Brutovsky and Daniel Novak; Title: Low Cost Rehabilitation System for Post-operation Exercises; Date of publication: Aug. 30, 2006; http://embc2006.njit.edu.

(Continued)

*Primary Examiner* — Daniel Wu
*Assistant Examiner* — Son M Tang
(74) *Attorney, Agent, or Firm* — Eric Karich

(57) ABSTRACT

A sensor device has an insole, a sensor body abutting the insole, pressure sensors operably mounted on the sensor body for generating a pressure data signal, and an accelerometer mounted on the insole for generating a movement data signal indicating the measuring movement of the insole. A transmitter is used for transmitting the pressure data signal and the movement data signal to a reporting device having a receiver for receiving the pressure data signal and the movement data signal. The reporting device further has a processor and a computer-readable medium for storing the pressure data signal and the movement data signal.

18 Claims, 15 Drawing Sheets

U.S. PATENT DOCUMENTS

| | | | |
|---|---|---|---|
| 5,980,472 | A | 11/1999 | Seyl |
| 6,032,530 | A | 3/2000 | Hock |
| 6,059,576 | A | 5/2000 | Brann |
| 6,122,846 | A | 9/2000 | Gray |
| 6,273,863 | B1 | 8/2001 | Avni et al. |
| 6,356,856 | B1 | 3/2002 | Damen et al. |
| 6,578,291 | B2 | 6/2003 | Hirsch et al. |
| 6,807,869 | B2 | 10/2004 | Farringdon et al. |
| 6,964,205 | B2 | 11/2005 | Papakostas et al. |
| 6,993,954 | B1 | 2/2006 | George et al. |
| 7,258,026 | B2 | 8/2007 | Papakostas et al. |
| 7,277,021 | B2 | 10/2007 | Beebe et al. |
| 7,355,519 | B2 * | 4/2008 | Grold et al. ................. 340/573.7 |
| 7,596,891 | B2 | 10/2009 | Carnes et al. |
| 7,607,243 | B2 | 10/2009 | Berner et al. |
| 8,280,681 | B2 * | 10/2012 | Vock et al. .................... 702/173 |
| 2003/0009308 | A1 * | 1/2003 | Kirtley .......................... 702/141 |
| 2003/0163287 | A1 * | 8/2003 | Vock et al. ..................... 702/187 |
| 2005/0261609 | A1 * | 11/2005 | Collings et al. ................ 600/592 |
| 2006/0122528 | A1 | 6/2006 | Gal |
| 2007/0049853 | A1 | 3/2007 | Adams et al. |
| 2007/0173903 | A1 * | 7/2007 | Goren et al. ..................... 607/49 |
| 2008/0108913 | A1 * | 5/2008 | Lengsfeld et al. ............. 600/595 |
| 2009/0137933 | A1 * | 5/2009 | Lieberman et al. ........... 600/595 |
| 2009/0264711 | A1 * | 10/2009 | Schuler et al. ................. 600/300 |
| 2010/0204616 | A1 | 8/2010 | Shears et al. |
| 2011/0013713 | A1 | 1/2011 | Li et al. |

FOREIGN PATENT DOCUMENTS

| | | |
|---|---|---|
| WO | WO 0110508 | 2/2001 |
| WO | WO2009112281 | 9/2009 |

OTHER PUBLICATIONS

Author: Unknown; Title: Tekscan: The Leader in Pressure Mapping; www.tekscan.com; Date: Unknown.

* cited by examiner

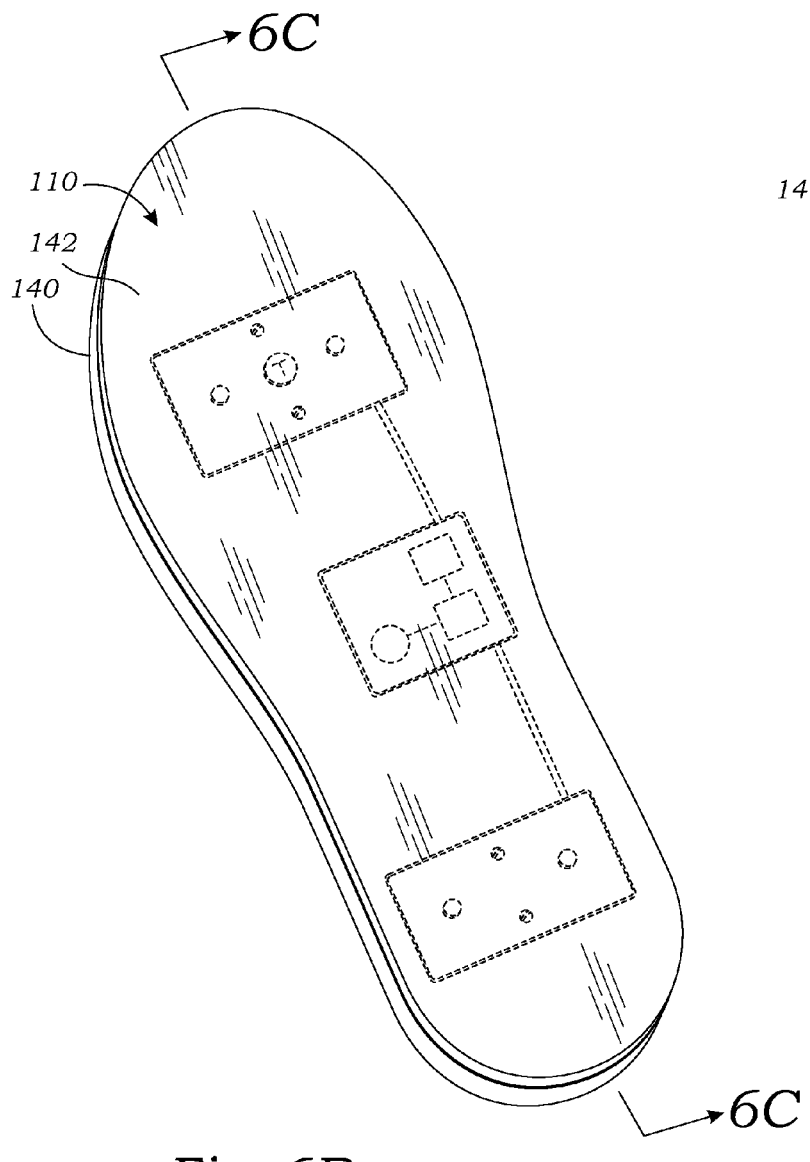
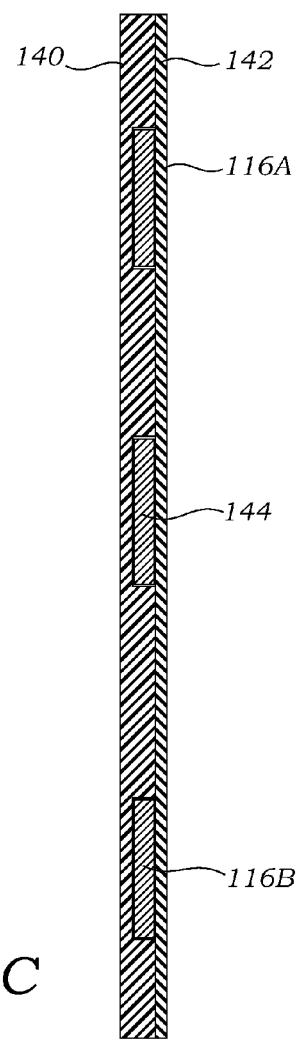
Fig. 6B
Fig. 6C

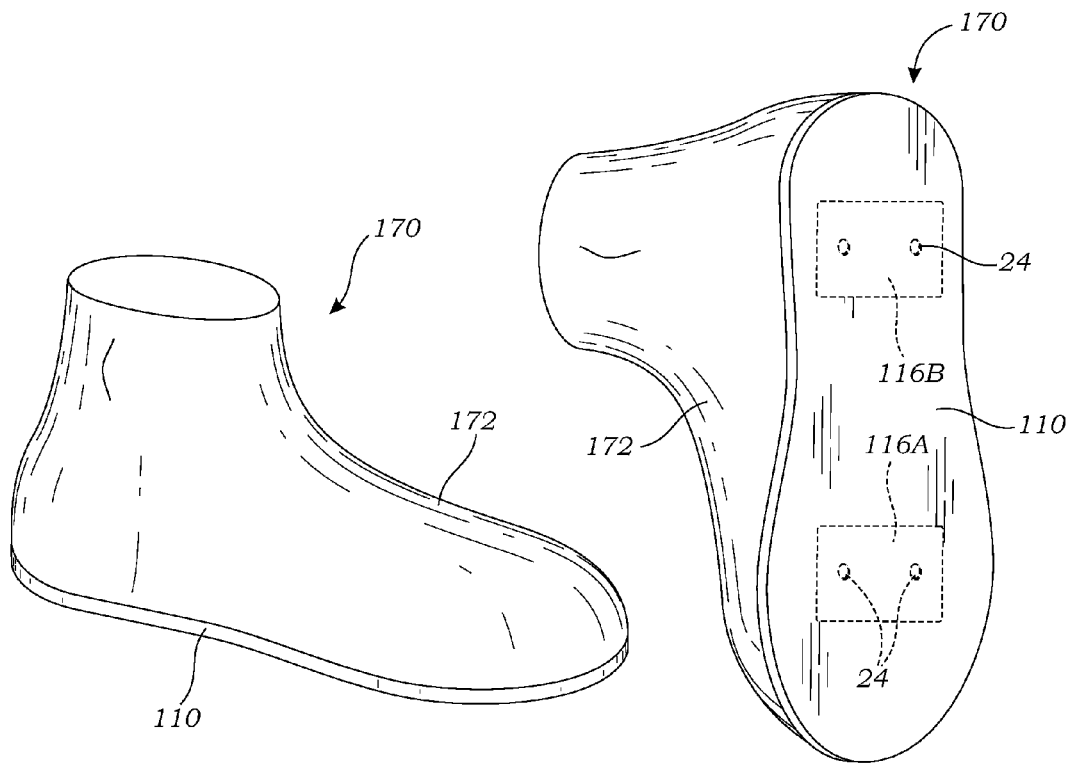
Fig. 8A
Fig. 8B
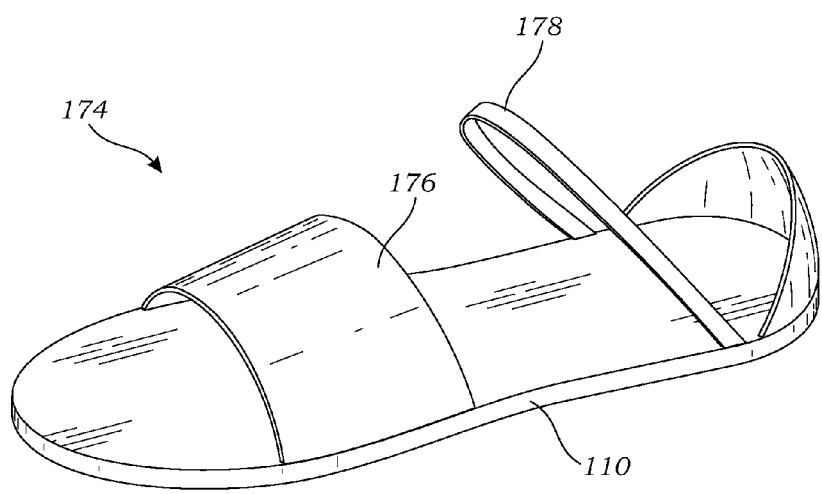
Fig. 9

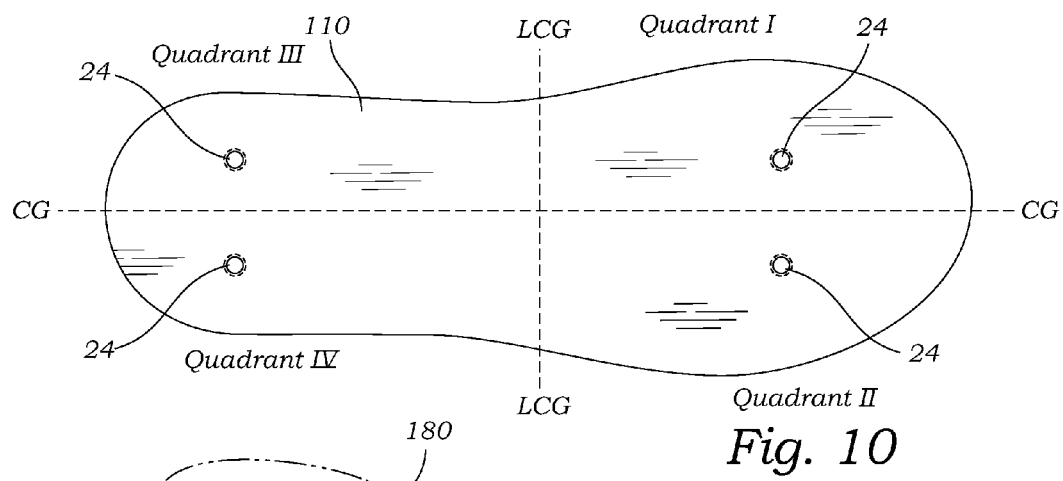
Fig. 10
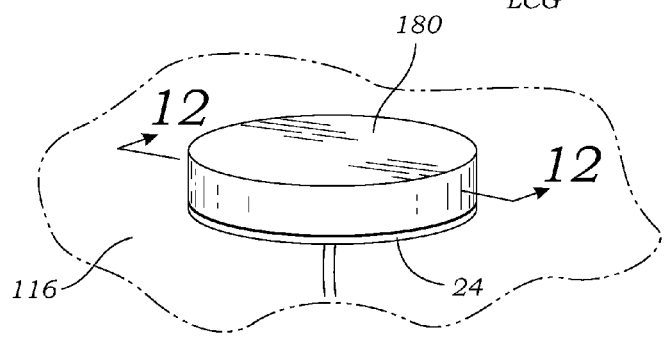
Fig. 11
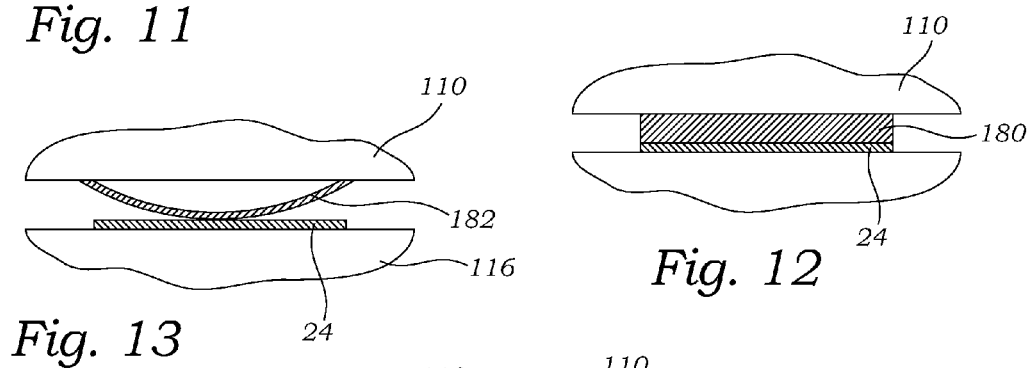
Fig. 12
Fig. 13
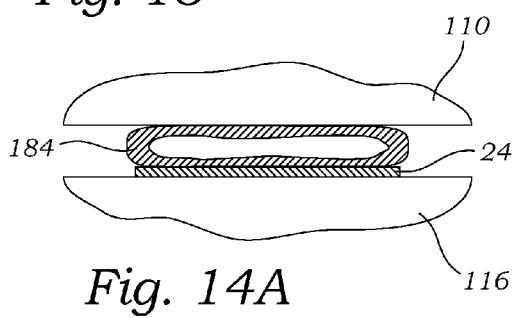
Fig. 14A
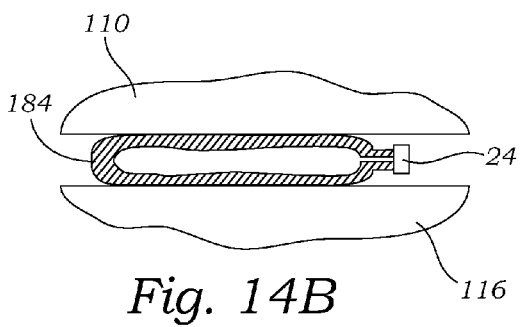
Fig. 14B

SENSOR DEVICE AND METHOD FOR MONITORING PHYSICAL STRESSES PLACED ON A USER

CROSS-REFERENCE TO RELATED APPLICATIONS

This application for a utility patent is a continuation-in-part of a previously filed utility patent, having the application Ser. No. 12/128,498, filed May 28, 2008 now U.S. Pat. No. 7,969,315.

STATEMENT REGARDING FEDERALLY SPONSORED RESEARCH

Not Applicable

BACKGROUND OF THE INVENTION

1. Field of the Invention

This invention relates generally to sensor devices, and more particularly to a sensor device and method for monitoring physical rehabilitation exercises and the like, and alerting the user if the exercises are being performed incorrectly.

2. Description of Related Art

There are various devices in the prior art that teach sensor devices for measuring pressure placed upon a user's foot for the purposes of assisting in rehabilitation of a user's leg following an injury.

Knotts et al., U.S. Pat. No. 5,107,854, teaches a slipper that includes a fluid chamber that enables weight sensing by a load monitor. When not enough weight is applied, or when too much weight is applied, a beeping sound is emitted to guide the patient in rehabilitating an injured leg.

Huberti, U.S. Pat. No. 5,042,504, teaches an insertable sole that includes plates having force sensors for determining a load placed upon the sole by a user. An amplifier and AC/DC converter generate a force signal that is received by a processor for generating audible and visual feedback via a piezo-beeper and display screen.

Gray, U.S. Pat. No. 5,269,081, teaches a force monitoring shoe that includes a spring, a sensor for sensing force applied to the spring, and a feedback mechanism that may include a beeper, flashing LEDs, a shocking element, vibrational (tactile) feedback.

Gray, U.S. Pat. No. 5,357,696, teaches a force monitoring shoe similar to the '081 patent, utilizing a force monitoring device to measure force exerted on the shoe, warn the patient (e.g., a beeper) if predetermined force levels are exceeded, and collect the accumulated data in a data gathering device. The pressure sensor may be a resistive sensor pad, and the patient alerting elements may include a wireless transmitter that transmits a signal to a separate unit that vibrates in response to exceeding recommended forces. The data gathering device may be a recorder, or a receiver in a doctor's office.

Schmidt et al., U.S. Pat. No. 5,619,186, teaches a rehabilitation device that measures force exerted on a sensor in a shoe for the purposes of guiding a patient in placing the correct amount of weight on an injured leg.

Schmidt et al., U.S. Pat. No. 5,408,873, teaches a similar foot force sensor that includes a special insole made of layers of relatively thin, planar, flexible dielectric material. Electrical contacts are interposed between the layers for sensing force.

Avni et al, U.S. Pat. No. 6,273,863, teaches a rehabilitation device that measures force exerted on a sensor in a shoe for the purposes of guiding a patient in placing the correct amount of weight on an injured leg.

Fullen et al., U.S. Pat. No. 5,323,650, teaches a rehabilitation device that includes a force sensor array adapted to be positioned in a shoe, a cable for connecting the force sensor array with an electronic circuit module that includes a CPU, RAM, ROM, and scanning circuitry for continuously electronically scanning the sensor array to determine instant force sensed by the sensors.

Gray, U.S. Pat. No. 6,122,846, teaches a force monitoring shoe similar to the other Gray patents described above. The shoe includes two semi-rigid plates, with a force sensor positioned therebetween. The force signals generated are transmitted via wireless to a reporting device that is separate from the shoe. The reporting device not only displays the readings, it may also be used to transmit the data to a remote computer for storage and analysis.

Beebe et al., U.S. Pat. No. 7,277,021, teaches a device for determining the wear of a sole of a shoe, to determine when the shoe is worn out and needs to be replaced. A control circuit connectable to first and second sensors compares the difference between the first and second signals to a threshold and generates an alert signal in response to the difference between the first and second signal meeting the threshold, thereby indicating that the shoe needs to be replaced, at which point an LED is illuminated.

There are various sensor devices that include accelerometers for various purposes. For example, Hirsch et al., U.S. Pat. No. 6,578,291, teaches a shoe having a built-in electronic wear indicator device that includes an accelerometer for measuring foot movement.

Damen et al., U.S. Pat. No. 6,356,856, teaches a system built into a shoe or measuring the speed of a person while running or walking. An acceleration sensor measures the acceleration in the forward direction and provides an acceleration signal which is amplified and subsequently sampled by analog to digital converter. The digital signal is processed by a microprocessor which executes an algorithm that determines the stride length and the stride duration from the digitized acceleration signal and calculates the speed and the distance traversed. The information thus obtained is transmitted by an RF transceiver to a watch or other device which includes a display which can be viewed by the runner or walker. The speed and distance traversed is displayed on the display, along with other useful information, such as average speed, maximum speed, total distance traversed, calories expended, and heart beat. Similar shoes are also shown in Huang, U.S. Pat. No. 5,875,571, Huang, U.S. Pat. No. 5,815,954, Hutchings, U.S. Pat. No. 5,724,265, and Huang, U.S. Pat. No. 5,661,916.

Cherdak, U.S. Pat. No. 5,452,269, teaches an athletic shoe which includes a timing device for measuring the amount of time the athletic shoe is off the ground and in air. The athletic shoe includes a notification device which can be operatively coupled to the timing device for notifying a wearer of the amount of time the athletic shoe is off the ground and in the air.

Wood, U.S. Pat. No. 5,373,651, teaches footwear adapted to measure the number and the force of steps that have been taken by the user during a predetermined interval. The wearer can subsequently transfer the step information into a computer for further analysis via an inductively coupled data link between the footwear and the computer.

Adams et al., U.S. 2007/0049853, teaches a compression device for a limb of a patient for applying a predetermined amount of pressure to the limb, and for reporting the pressure actually applied to the limb via an external reporting device.

The compression device includes an inflatable sleeve arranged to surround the limb, and a conduit attached to the sleeve arranged to deliver fluid to the sleeve for providing the pressure. A control system controls fluid flow in the device and a memory arranged to store gathered data relating to use of the device.

The above-described references are hereby incorporated by reference in full.

SUMMARY OF THE INVENTION

The present invention teaches certain benefits in construction and use which give rise to the objectives described below.

The present invention provides a sensor device having an insole, a sensor body abutting the insole, and pressure sensors operably mounted on the sensor body for sensing pressure against the insole, the pressure sensors functioning to generate a pressure data signal indicating the pressures sensed. An accelerometer is mounted on the insole for generating a movement data signal indicating the measuring movement of the insole. The sensor device further includes a transmitter for transmitting the pressure data signal and the movement data signal to a reporting device having a receiver for receiving the pressure data signal and the movement data signal. The reporting device further includes a processor and a computer-readable medium for storing the pressure data signal and the movement data signal.

A primary objective of the present invention is to provide a sensor device having advantages not taught by the prior art.

Another objective is to provide a sensor device that can measure both pressure and movement, so guide users through rehabilitation exercises and to also record the data for analysis by doctors or other specialists.

A further objective is to provide a sensor device that is inexpensive to manufacture, that can be readily adapted for use with different shoe sizes, that can quickly and accurately measure the user's movements in any location.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the present invention. In such drawings:

FIG. 6B is a perspective view thereof once the sensor device has been assembled;

FIG. 6C is a sectional view thereof along lines 6C-6C in FIG. 6B;

FIG. 8A is a perspective view of a slipper device that incorporates the sensor device of FIG. 5;

FIG. 8B is a bottom perspective view thereof;

FIG. 9 is a perspective view of a sandal device that incorporates the sensor device of FIG. 5;

FIG. 10 is a top plan view of the insole, illustrating one embodiment of how the pressure sensors are arranged on the insole;

FIG. 11 is a perspective view of one embodiment of a force concentrator operably mounted on one of the pressure sensors of FIG. 5;

FIG. 12 is a sectional view taken along lines 12-12 in FIG. 11, illustrating how the force concentrator operates for concentrate forces onto the pressure sensor;

FIG. 13 is a sectional view of another embodiment of the force concentrator;

FIG. 14A is a sectional view of third embodiment of the force concentrator, wherein the force concentrator includes a bladder;

FIG. 14B is a sectional view of fourth embodiment of the force concentrator, wherein the force concentrator includes an alternative bladder that is operably connected to a MEMS pressure sensor;

DETAILED DESCRIPTION OF THE INVENTION

The above-described drawing figures illustrate the invention, a sensor system 10 for monitoring physical stresses placed upon an injured leg, as well as movements of the leg by a user 12 during physical rehabilitation exercises and the like, and for providing an alert in the event that force levels on the leg and/or the movement of the leg exceed predetermined levels of force and/or range of motion.

Figure 1:
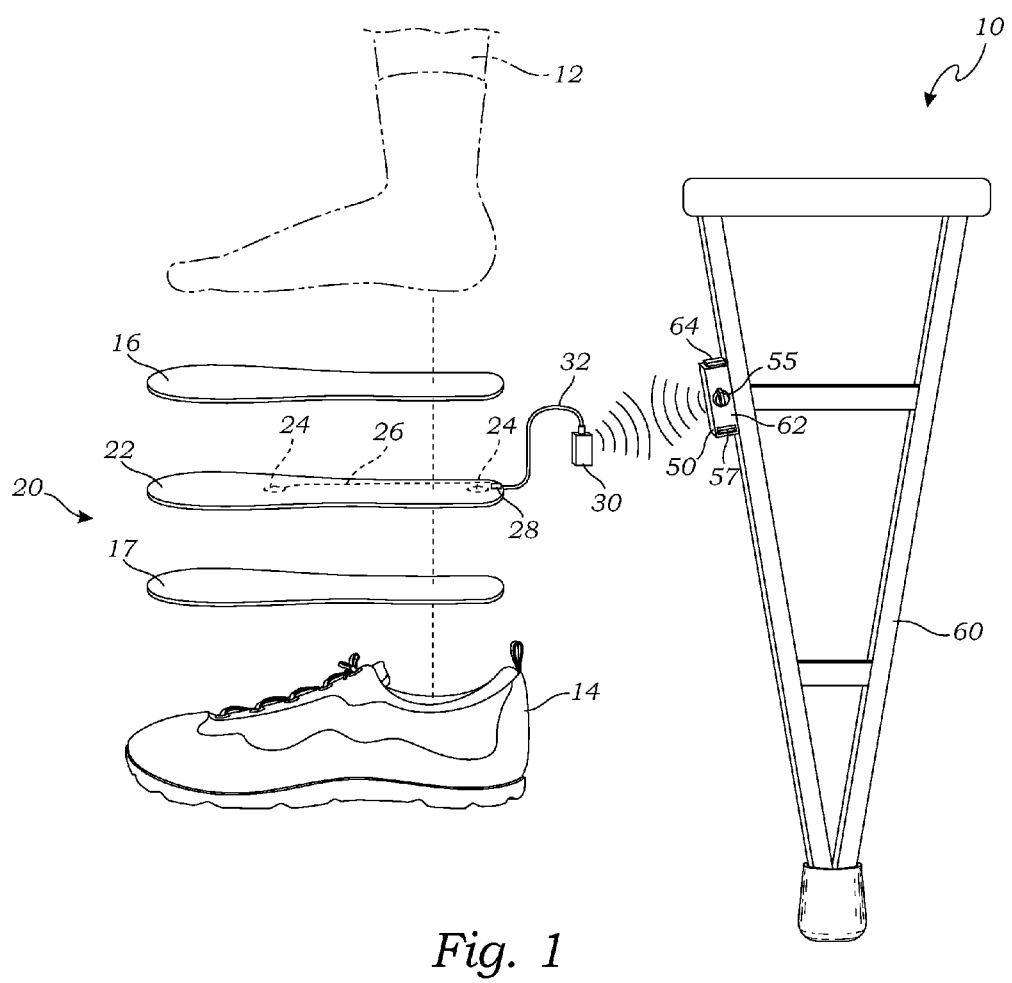
FIG. 1 is a perspective view of a sensor system according to one embodiment of the present invention, the sensor system including a sensor device and a reporting device for receiving data from the sensor device.
Figure 2:
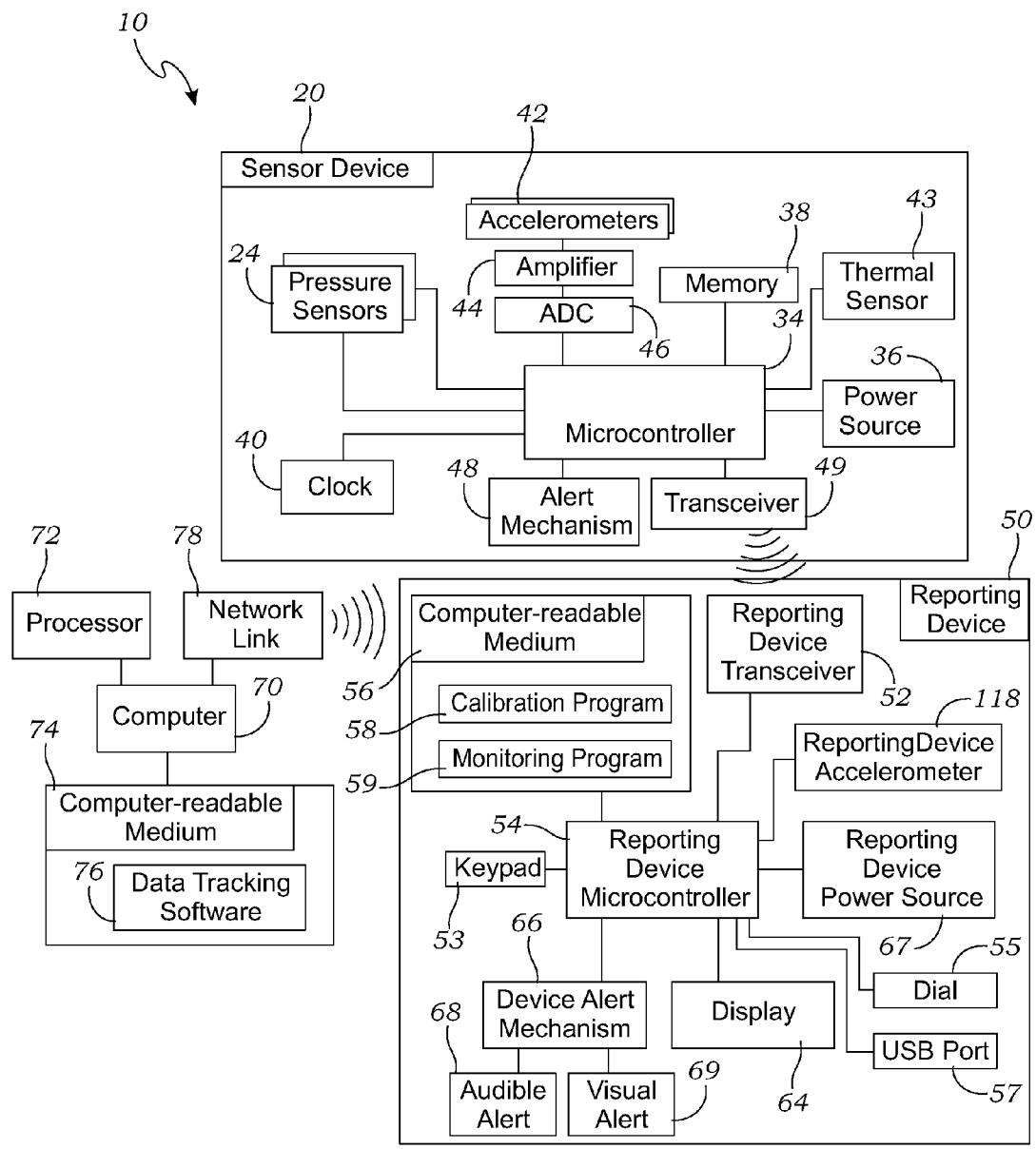
FIG. 2 is a block diagram thereof.

FIG. 1 is an exploded perspective view of the sensor system 10 according to one embodiment of the present invention, and FIG. 2 is a block diagram thereof. As shown in FIGS. 1 and 2, the sensor system 10 may include a sensor device 20 and a separate reporting device 50. An alternative embodiments, however, the sensor system 10 may also be in the form of a single device.

The sensor device 20 may include a sensor body 22 adapted to be positioned within a shoe 14. Pressure sensors 24 are operably mounted on the sensor body 22 for sensing pressure placed upon the sensor device 20. The pressure sensors 24 function to generate a pressure data signal indicating the pressures sensed. In the embodiment of FIG. 1, the sensor device 20 is positioned between an insole 16 and a protective layer 17. The insole 16 and the protective layer 17 provide a comfortable bearing surface for the user 12, as well as protect the sensor body 22 from inadvertent damage.

The sensor body 22 may be constructed of a flexible printed circuit board (PCB) having two of the pressure sensors 24 (or any other number of pressure sensors, as determined suitable by one skilled in the art) mounted thereupon and electrically conductive leads 26 connecting the two pressure sensors 24 to a wire mounting point 28. The flexible printed circuit board may be formed of any suitable substrate (e.g., plastic, polyester, etc.) using techniques that are known in the art.

The sensor body 22 may further include a rigid electronics housing 30 adapted to be mounted on an exterior surface of the shoe 14, and an electrically conductive wire 32 extending from the wire mounting point 28 of the sensor body 22 to the rigid electronics housing 30. The rigid electronics housing 30 may include a processor 34 such as a microcontroller, a power source 36, a memory 38, and a clock 40. The term "microcontroller" is hereby defined to include any processors, chip(s), circuit(s), and/or other devices known to those skilled in the art that function to operably connect and control the various elements of the sensor device 20 as described herein. The memory 38 may include a computer readable medium for storing programs, as described below, and/or an electronic storage (e.g., RAM, ROM, etc.) for storing predetermined storing threshold force levels, and/or readings received from the pressure sensors 24.

In one embodiment, the rigid electronics housing 30 includes the alert mechanism 48, such as a beeper, buzzer, flashing light, etc., so that the sensor device 20 can not only received the readings from the pressure sensors 24, it can also alert the user 12 when the pressure sensors 24 report pressure readings greater than the predetermined threshold force levels. In the embodiment of FIGS. 1 and 2, however, the pressure readings are reported to the reporting device 50 for analysis and for alerting the user 12 via the reporting device 50.

The rigid electronics housing 30 of the sensor device 20 may further include an accelerometer 42 operably connected to the microcontroller 34 through an amplifier 44 and an analog to digital converter (ADC) 46. The accelerometer 42 tracks the movements of the foot of the user 12. The history of movement of the foot of the user 12, in conjunction with the pressure sensor 24 readings, create a detailed history of the user's movements that enable a doctor to later analyze the data and determine the user's movements and how the user 12 may have been correctly and/or incorrectly exerting the leg. For example, if the user 12 routinely places too much stress on the leg while climbing stairs, the doctor could determine this fact and advise the user 12 to be more careful on stairs, or to avoid them entirely if necessary.

In the embodiment of FIGS. 1 and 2, the sensor device 20 may further include a transceiver 49 for transmitting the pressure data signal (and/or data from the accelerometer 42) to the reporting device 50. The term "transceiver" as used in this application is hereby defined to include any form of wirelessly sending and/or receiving information, including but not limited to any form of wireless communication, transponder, and/or other form of wireless communications device and/or connection. Other forms of connection, for example, a USB port 57 or similar port, may enable a wired connection to the reporting device 50 and/or other computer devices.

As illustrated in FIGS. 1 and 2, the reporting device 50 may include a reporting device transceiver 52 for receiving the pressure data signal. As discussed above, the connection between the transceiver 49 and the reporting device transceiver 52 is preferably wireless; however, in alternative embodiments it may be a wired connection.

The reporting device 50 may include a reporting device microcontroller 54 operably connected to computer-readable medium 56. The computer-readable medium 56 includes a calibration program 58, a monitoring program 59, and any other programs and/or software necessary for the function of the reporting device 50. The calibration program 58 functions to store threshold force levels. In one embodiment, for example, when a user 12 receives the reporting device 50, he or she first inputs his or her weight, and/or any other pertinent information. The information may be downloaded electronically through the USB port 57, entered via a keypad 53, or otherwise inputted via mechanisms well known in the art.

The user 12 may also input what percentage of weight he or she should place upon the leg, or some other measure of stress advised by a doctor. In one embodiment, a percentage of stress is inputted by turning a dial 55. In another embodiment, a specific amount of force may be specified, and downloaded into the reporting device 50 using any mechanism described herein, or any alternative mechanism known to those skilled in the art.

The calibration program 58 functions to analyze the data that is inputted (e.g., the users weight and percentage of weight advised by doctor, direct input of force level, etc.) and determine the threshold force levels that are acceptable, and the threshold force levels that will trigger of alert. It is possible that the reporting device 50 only analyze a single threshold force level, such as a maximum pressure received, or it may track multiple threshold force levels, various forms of averages of forces detected, and/or may also track various forms of torque, sustained pressure, instant pressure, or more specific forces that may very be particularly damaging to a person's leg. Such parameters may be devised by those skilled in the art, and any such method should be considered within the scope of the present invention.

The monitoring program 59 determines if the pressure data signal indicates that the pressure exceeds one of the threshold force levels. As discussed above, treating doctors and others skilled in the art may devised many alternative methods of analyzing the threshold force levels to determine when a warning is required. In its simplest form, the monitoring program 59 merely measures forces sensed by the pressure sensors 24, and sounds an alert if those forces exceed a certain level. In alternative embodiments, a more sophisticated analysis might be used, and such alternatives should be considered within the scope of the present invention.

The reporting device microcontroller 54 is operably connected to a reporting device alert mechanism 66 for alerting the user 12 when the threshold force levels are exceeded. In one embodiment, the reporting device alert mechanism 66 may include an audible alert 68 such as a speaker for admitting a warning, a buzzer, or any other form of audible alert known to one skilled in the art. In another embodiment, the reporting device alert mechanism may include a visual alert 69 such as a plurality of LEDs or other visual display elements. The visual alert 69 may also include data displayed on a display 64 (e.g., an LCD screen, LED display, etc.). Various other forms of alert mechanisms may also be included, including vibrating elements, electronic reporting elements (e.g., e-mail, instant message, etc.), flashing lights, sirens, and/or any other alert mechanisms known in the art.

In the embodiment of FIG. 1, a reporting device housing 62 containing the reporting device 50 is operably mounted on a crutch 60. The sensor device 20 is operably positioned in the shoe 14 worn by the user 12, and when the user 12 walks using the crutch 60, the reporting device 50 is maintained proximate to both the user 12 and the shoe 14. When the user 12 puts too much weight on a leg, the readings from the pressure sensors 24 are transmitted via the transceiver 49 of the sensor device 20 to the reporting device transceiver 52 of the reporting device 50. When the monitoring program 59 determines that the force levels reported exceed the acceptable threshold force levels, the device alert mechanism 66 triggers an alert, such as the audible alert 68 (e.g., siren or beeping sound), and/or the visual alert 69 (e.g., LEDs flashing a warning).

The reporting device 50 may be powered by a reporting device power source 67 (e.g., battery, solar cell, or any other source of power suitable for powering the reporting device 50) operably connected to the reporting device microcontroller 54.

Figure 3:
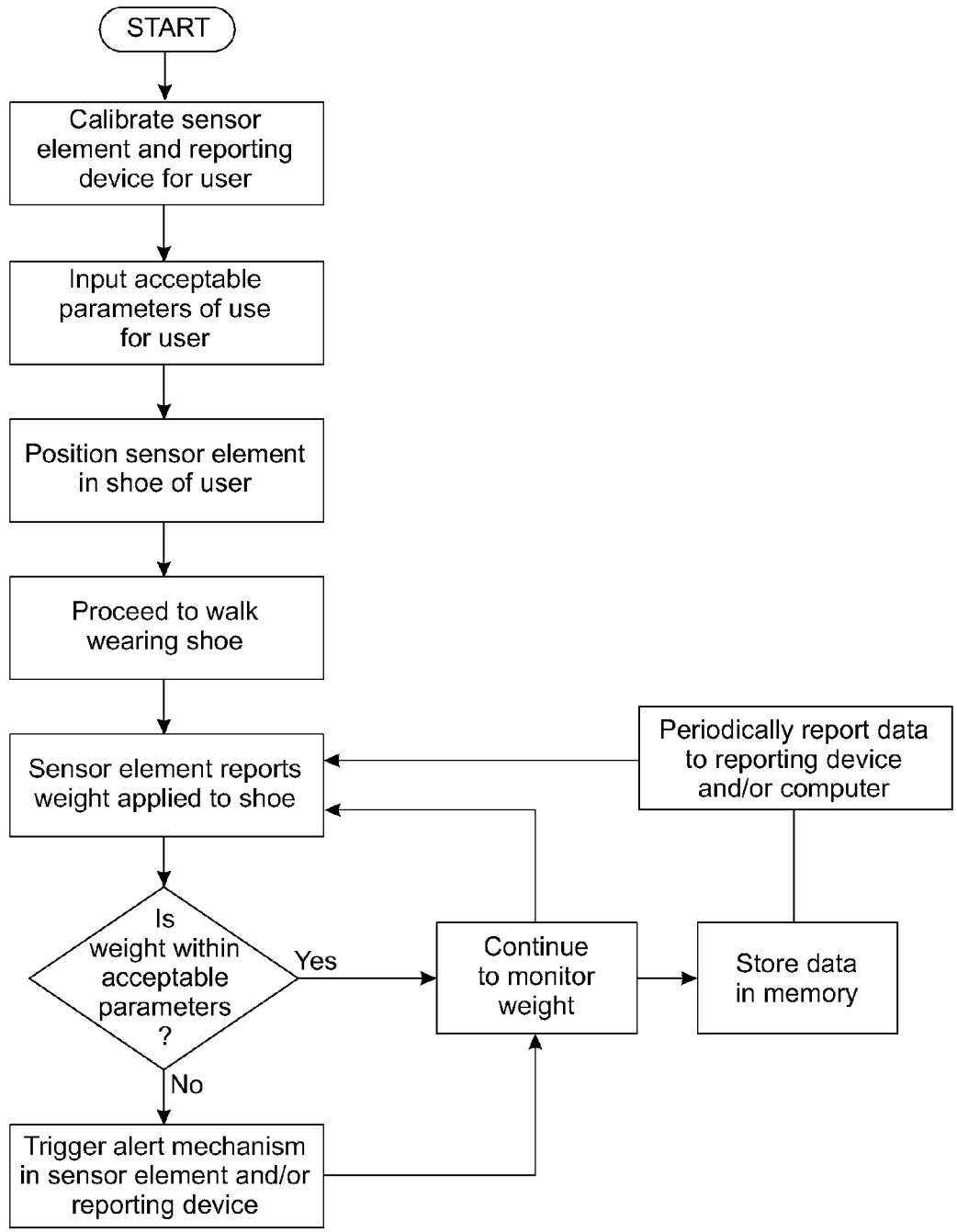
FIG. 3 is a flow diagram of the operation of the sensor system for alerting a user when pressure on the sensor device exceeds predetermined thresholds.

FIG. 3 is a flow diagram of the operation of the sensor system 10 for monitoring the physical stresses placed on the user 12 (such as his or her leg) and alerting the user 12 if the stresses exceed the predetermined threshold level. As illustrated in FIG. 3, the method includes the step of first providing the sensor device 20 described above.

The sensor system 10 of FIGS. 1 and 2 is first calibrated using the calibration program 58 described above. Relevant data, such as the users weight, is transferred to the reporting device 50 as discussed above. Acceptable force parameters, specific treatment parameters provided by a doctor, and/or any other data and/or treatment options may also be transferred. In one embodiment, as illustrated in FIG. 1, the dial 55 of the reporting device 50 is turned to the percentage of force that is recommended by the doctor. The predetermined threshold force levels that should not be exceeded are determined and stored.

Once calibrated, the sensor device 20 is operably positioned so that the pressure sensors 24 sense the stresses placed upon the user 12 (such as the user's leg). In the embodiment of FIG. 1, the sensor device 20 may be placed inside the shoe 14 between the insole 16 and the protective layer 17, or otherwise positioned in or on the shoe 14 for sensing pressures placed upon the shoe 14 by the user 12.

The user 12 then walks about, while wearing the shoe 14 (or other device containing the sensor system 10), and the sensor system 10 monitors the pressure data signal to determine if the pressure exceeds one of the threshold force levels. The user 12 (and/or the doctor, physical rehabilitation expert, etc.) is then alerted if the threshold force levels are exceeded, as discussed in greater detail above. If the user 12 is walking across the room, and he or she receives a warning signal, he or she will know to adjust his or her walk so that he or she is only exerting a suitable amount of stress upon the leg. If the user 12 is walking up stairs, and receives a warning, he or she will know to be more careful in climbing the stairs, so that he or she is not placed too much strain upon the leg.

In one embodiment, as illustrated in FIG. 2, the sensor system 10 further includes a computer 70 that includes a processor 72 and a computer readable medium 74. The computer readable medium 74 includes a data tracking software 76 that operably interacts with the reporting device 50 via a network link 78. The network link 78 may be any form of wired or wireless network connection, either direct or via the Internet, so that the data tracking software 76 can interact with the reporting device 50. The pressure data signal and/or any alerts received from the sensor device 20 and/or reported to the reporting device 50 are directed to the computer 70 for analysis using the data tracking software 76. Data from the accelerometer 42 may also be reported, so that the pressure data and alerts may be placed into context with the user's movements.

For example, the user's doctor may analyze the reported data and/or alerts to determine whether the user 12 is correctly following his or her exercise regime, and/or whether or not he or she is over-exerting himself or herself. The doctor might also determine whether the user 12 is prone to overstressing his or her leg during certain activities, such as climbing stairs, walking, engaging in activities at certain times of day, or otherwise. Once the doctor has been alerted to this situation, he or she can warn the user 12 against certain activities, or were in the user 12 to be more careful in these activities. The doctor might also determine from the collected data, that the user 12 is not exercising his or her leg enough, and the doctor might recommend that the user 12 get more exercise, and engage in more stressful activity.

Figure 4:
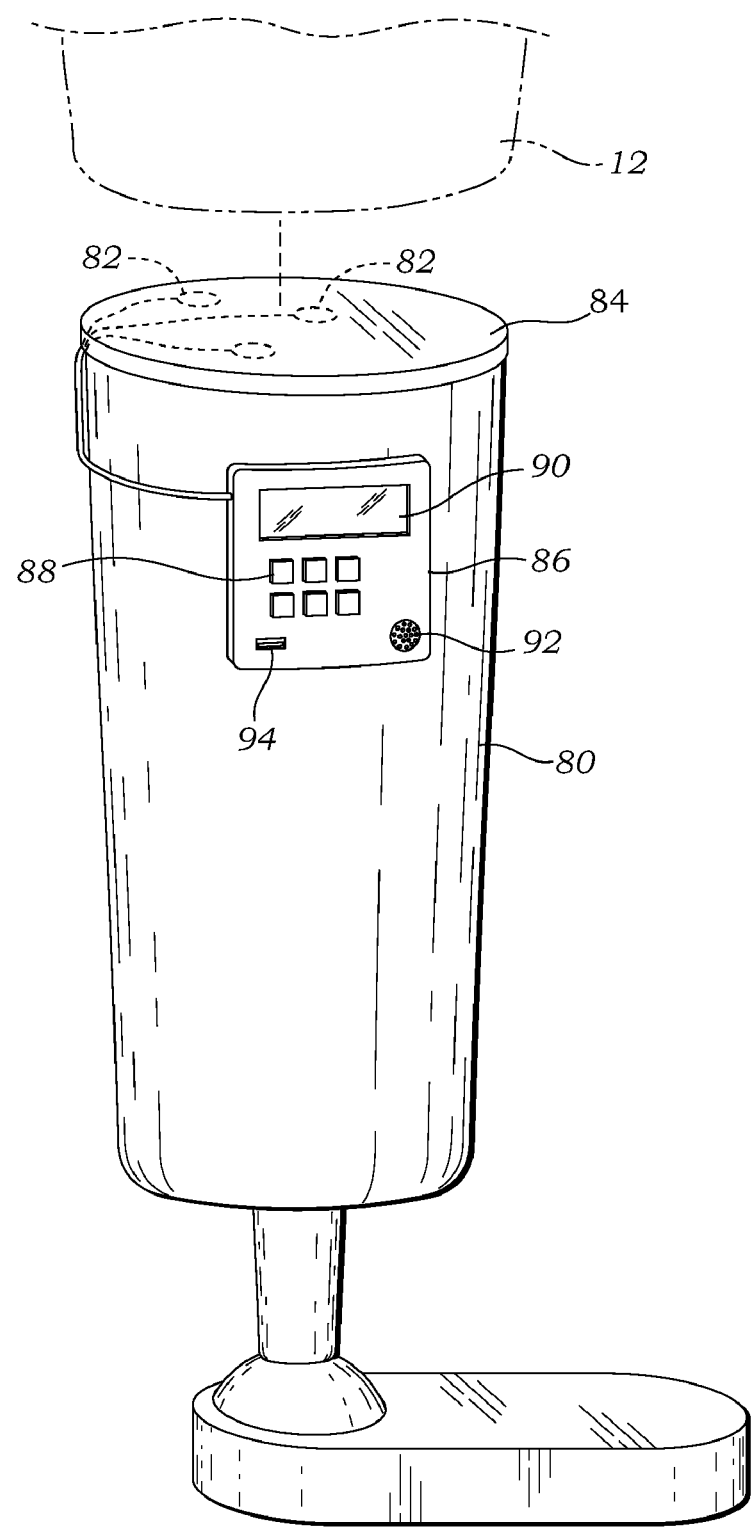
FIG. 4 is perspective view of a prosthesis leg that includes an alternative embodiment of the sensor system.

FIG. 4 is perspective view of a prosthesis leg 80 that includes an alternative embodiment of the sensor system 10. In this embodiment, the prosthesis leg 80 includes sensors 82 and batted in a pad 84, and a reporting device 86 built into the prosthesis leg 80. The reporting device 86 may include control buttons 88 for controlling the operation of the reporting device 86, a displaying 90 for displaying information and for enabling calibration of the device 86, a speaker 92 for sounding the alert, and port 94 (e.g., a USB port, or other data port) for enabling the reporting device 86 to be connected to a computer for calibration and data downloads. The prosthesis leg 80 may further include any of the elements described above, the port 94 may be replaced or supplemented with the transceiver 49 and/or any other form of data transfer mechanism.

In the embodiment of FIG. 4, the prosthesis leg 80 incorporates the elements described above for tracking and the use of the leg 80 so that the user 12 does not place too much strain on his or her leg well using a prosthesis leg 80. While one type of prosthesis is illustrated herein, any form of prosthesis may incorporate the sensors 82 and other elements of the invention for tracking and recording stresses placed upon the user 12 by the prosthesis, and for sounding or otherwise providing an alert in the event that the sensors recorded too great of a strain upon the user 12. As discussed above, this data may also be compiled and analyzed with the computer 77 the doctor may determine whether the prosthesis is being used correctly, or whether the user 12 may need to modify his or her behavior to prevent potential injury.

Figure 5:
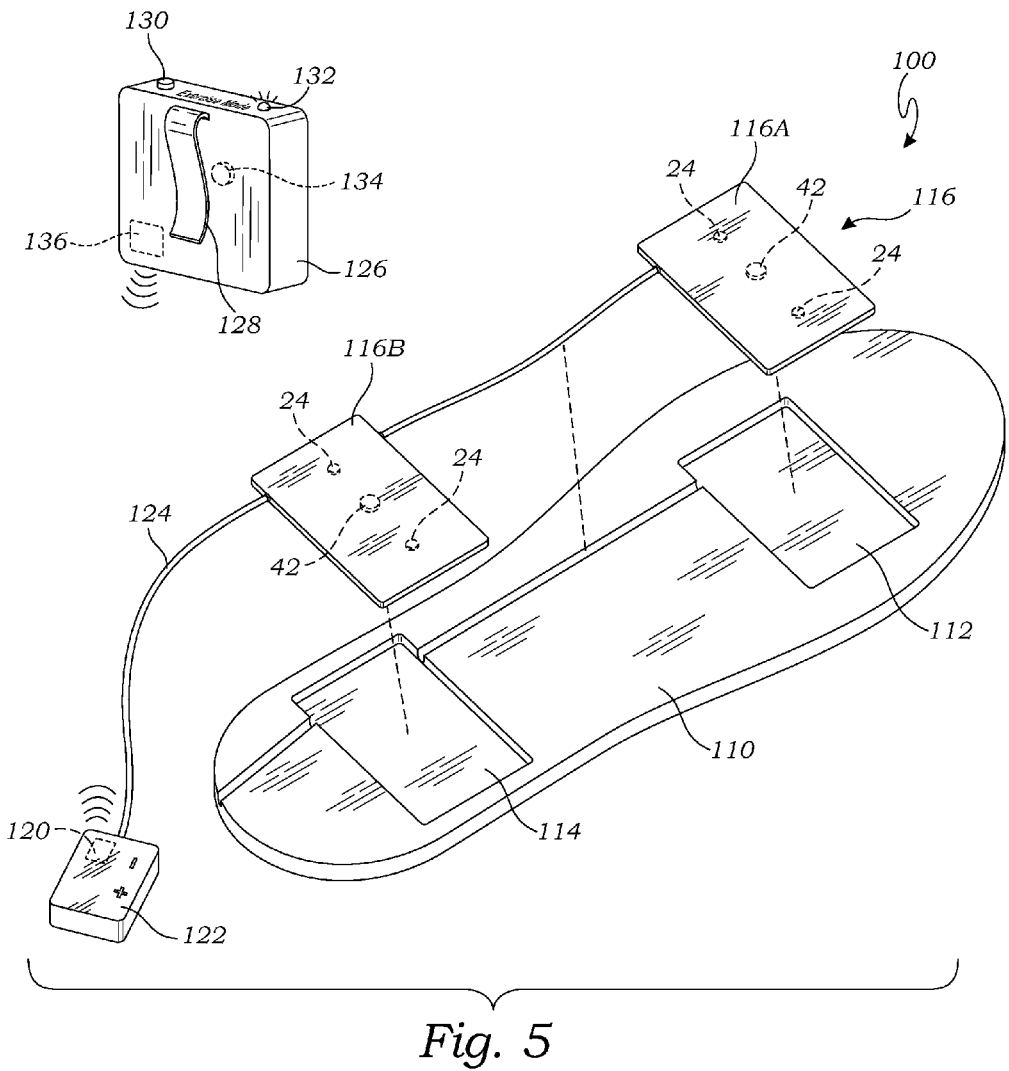
FIG. 5 is an exploded perspective view of another embodiment of the sensor device, including a semi-rigid planar insole adapted to receive a pair of sensor boards that include the pressure sensors.

FIG. 5 is an exploded perspective view of another embodiment of the sensor device 100, including an insole 110 that may be semi-rigid, planar, and may be adapted to fit within a shoe (or other device) for receiving a sensor body 116 abutting the insole 110. In the present embodiment, the sensor body 116 includes a pair of sensor boards, a front sensor board 116A and a rear sensor board 116B, that each include two of the pressure sensors 24. The sensor boards 116 may be flexible printed circuit boards (PCB) that are able to flex somewhat to avoid damage during use. In alternative embodiments, one or another number of sensors may be used, or a sheet of sensors may be used to sense pressure across substantially all of the user's foot.

In the embodiment of FIG. 5, the insole 110 is shaped to fit within the shoe, and may vary in size and width according to the different shoe sizes of the various users. The insole 110 may include a front recess 112 positioned under the ball of the user's foot, and a rear recess 114 positioned under the heel of the user's foot. In assembly, the front sensor board 116A is positioned in the front recess 112 and the rear sensor board 116B is positioned in the rear recess 114, so that the pressure sensors are properly positioned on the user's foot. The positioning is discussed in greater detail below, and illustrated in FIG. 10.

When the user applies pressure to his or her leg, the insole 110 and the sensor boards 116 are compressed together, thereby applying pressure to the pressure sensors 24. Various intermediaries, force concentrators, and other elements may also be included, as discussed in greater detail below.

The insole 110 may further include an accelerometer 42 (or multiple accelerometers, as required by one skilled in the art). In this embodiment, each of the sensor boards includes an accelerometer 42, which may be mounted between the pressure sensors (or in other suitable locations). The accelerometers 42 function to generate a movement data signal indicating the measuring movement of the insole 110. The particular number of accelerometers 42 (or suitable additional electronics devices) is not important, as long as they are collectively able to measure the three dimensional movement of the insole 110. The term "accelerometer" is hereby defined to include any electronics components that perform these functions, including gyros and related products, such as a 3-axis low power gyro sold by VTI Technologies, Inc., under the designation CMR3000-D01.

As discussed above, a transmitter 120, such as the transceivers discussed above, or any other suitable data transfer mechanism, is operably connected for transmitting the pressure data signal and the movement data signal to the reporting device 126. A battery pack 122 may also be operably attached to the sensor boards with a power wire 124 for providing power to the sensor boards. In other embodiments, the power source, such as a battery 36, may be mounted in the insole 110 and/or sensor body 116, some embodiments of which are described below.

Also illustrated in FIG. 5, the sensor device 100 may further include another embodiment of a reporting device 126 that is adapted to be worn on the user's body, such as via a belt clip 128. The term belt clip 128 is defined to include any form of clip, hanger, or other form or attachment device known in the art for attaching a small device of this sort to a user's belt, pants, or other clothing around his or her midsection.

The reporting device 126 may include an exercise mode button 130 (defined to include any form of switch or activation device known in the art) for initiating an exercise mode of operation, as described in greater detail below. The reporting device 126 may further include an exercise mode LED 132 (defined to include any form of illumination device, bulb, etc.) for visually indicating that the reporting device 126 is in exercise mode. It may also include additional indicators (not shown), for indicating other modes of operation, such as a passive mode (when not in exercise mode), or other modes devised by those skilled in the art.

The reporting device 126 may further include a reporting device accelerometer 134, as also illustrated in FIG. 2, for measuring movement of the reporting device 126. The benefits of this construction, and methods of use, are described in greater detail below. A reporting device transmitter 136 is used to communicate with the sensor device 100, as described above.

Figure 6A:
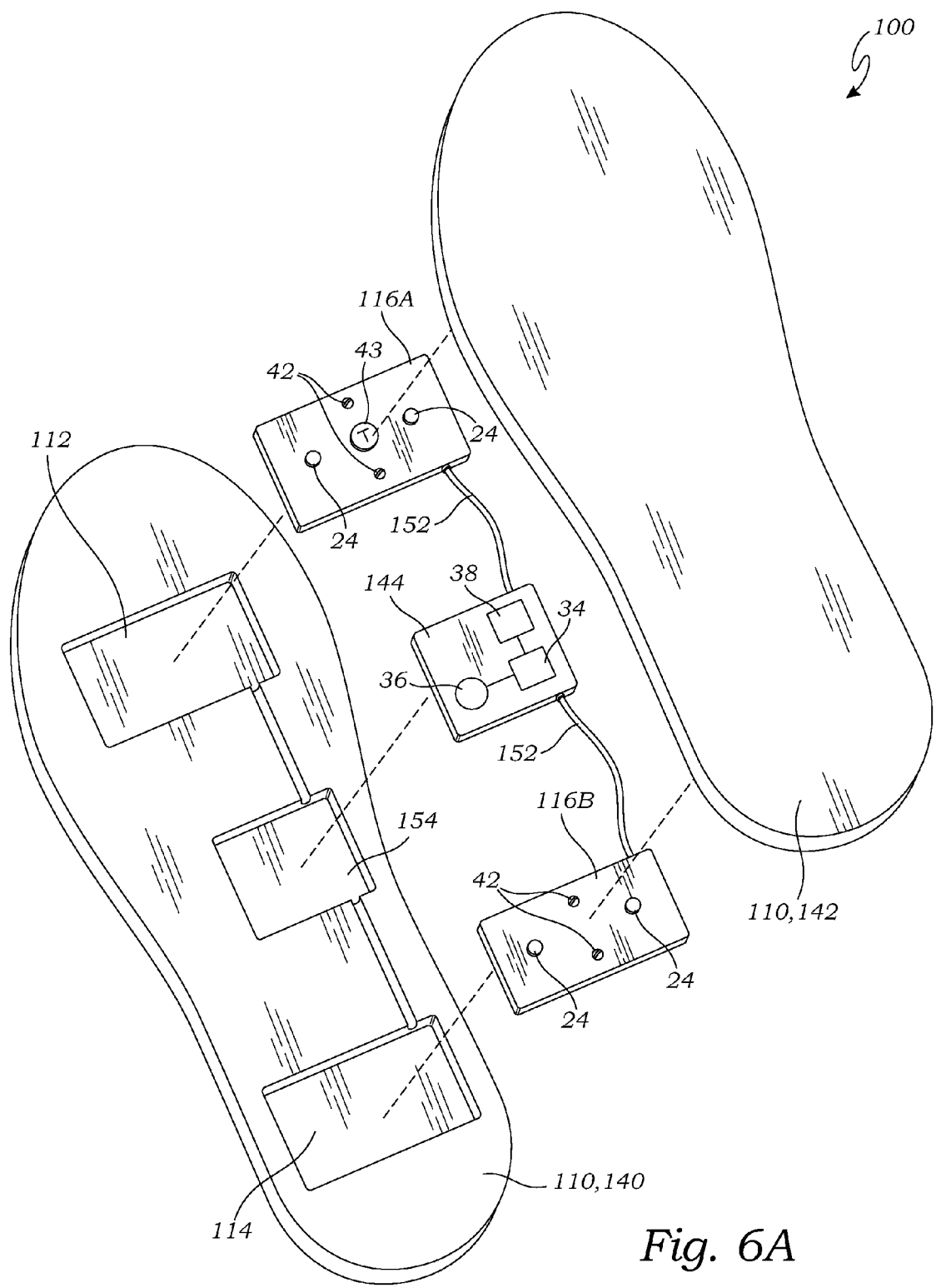
FIG. 6A is an exploded perspective view of yet another embodiment of the sensor device.

FIGS. 6A-6C illustrate another embodiment of the sensor device 100. In this embodiment, the insole 110 includes first and second layers 140 and 142 that together sandwich the sensor boards 116 therebetween. In this embodiment, a central board 144 includes the battery 36, the processor 34, the memory 38, and the transmitter 120, and is operably connected with the sensor boards 116 with electrical connectors 152. The central board 144 may be mounted in an arch recess 154 of the insole 110. The arch recess 154 is positioned under the arch of the user's foot, so that the central board 144 is protected from impacts of the user's foot upon the insole 110, most powerful at the ball and the heel of the user's foot.

Also illustrated in FIGS. 6A-6C, the sensor boards 116 may further include a temperature sensor 43 for measuring the temperature of the user's foot, preferable in the region of the toes. The temperature of the user's toes (or other region of the foot) provides important information about the health of the foot, and unusual temperatures may indicate certain medical conditions. Reduced temperatures in the region of the user's toes, for example, may indicate diabetes.

Figure 7:
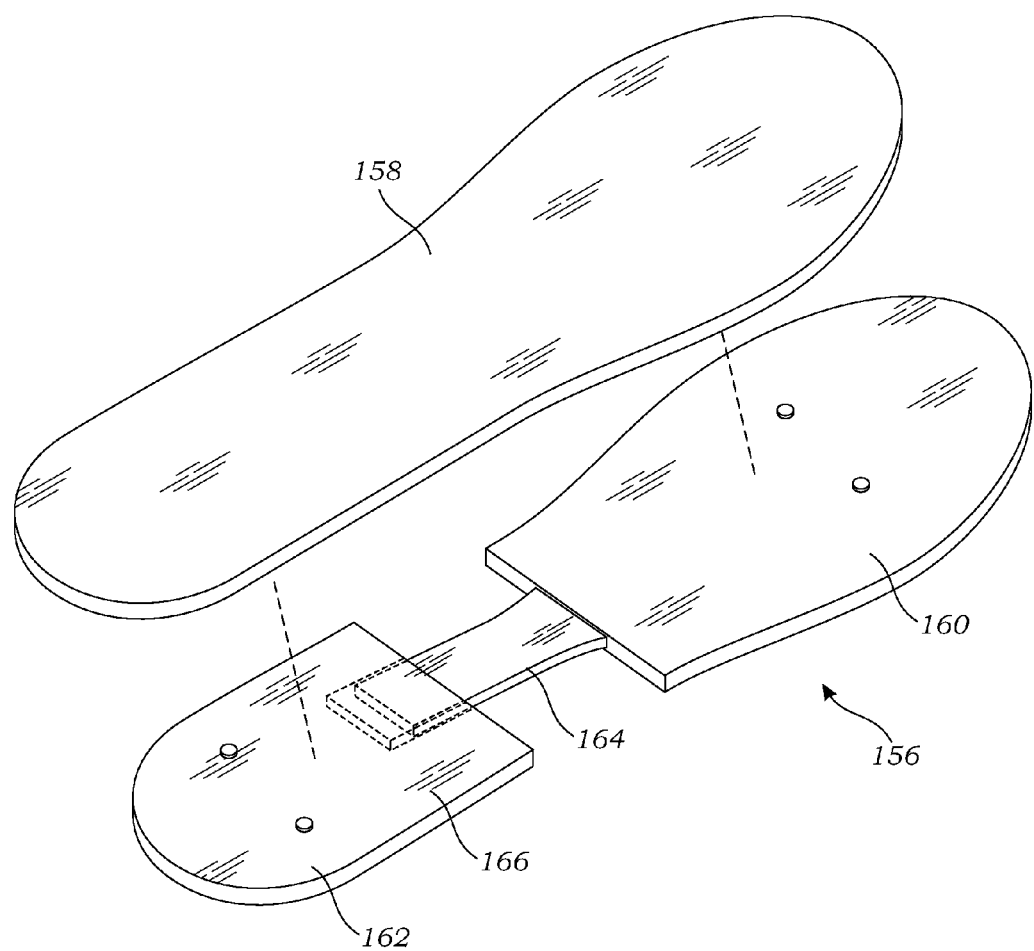
FIG. 7 is an exploded perspective view of yet another embodiment of the sensor device, illustrating an adjustable sensor platform.

FIG. 7 is an exploded perspective view of yet another embodiment of the sensor device 100, illustrating an adjustable sensor platform 156. In this embodiment, the insole 110 includes the adjustable sensor platform 156 and may include a protective upper layer 158 that is semi-rigid, planar, and adapted to protect the sensor platform 156. In this embodiment, the sensor platform 156 includes a forward portion 160 and a rearward portion 162 connected by a tab portion 164 that telescopically engages an adjustment slot 166. The various electronics components described above are built into the forward and rearward portions 160 and 162, while the tab portion 164 and slot 166 enable the size of the adjustable sensor platform 156 may be adjusted to fit different shoe sizes. While the protective upper layer 158 cannot be adjusted, it may be selected based upon the size required by the user.

FIG. 8A is a perspective view of a slipper device 170 that incorporates the sensor device 100 of FIG. 5, and FIG. 8B is a bottom perspective view thereof. As illustrated in FIGS. 8A and 8B, in one embodiment the insole 110 of FIG. 5 may form the sole of a slipper, and may include a flexible slipper upper 172 made of fabric or other suitable material. A comfortable slipper of this construction is well suited for wear around a house, hospital, or any location where rehabilitation is performed.

FIG. 9 is a perspective view of a sandal device 174 that incorporates the sensor device 100 of FIG. 5. The sandal device 174 may include a forward strap 176 and a rear strap 178 for securing the sensor device 100 onto the user's foot.

FIG. 10 is a top plan view of the insole 110, illustrating one embodiment of how the pressure sensors 24 are arranged on the insole 110. In the embodiment of FIG. 10, each of the four pressure sensors 24 are arranged in one of four quadrants formed by a longitudinal center of gravity CG and a lateral center of gravity LCG. The longitudinal center of gravity CG is formed along the long axis of the foot, at the center of balance when the user is standing stationary. The lateral center of gravity LCG is formed perpendicular to the longitudinal center of gravity CG and between the toes and the heel, where the user's center of gravity when standing stationary. Diligent experimentation has shown that distributing the pressure sensors 24 in each of the four quadrants provides superior results to other sensor arrangements. The use of this data is discussed in greater detail below, in conjunction with the discussion of FIGS. 19-21.

FIG. 11 is a perspective view of one embodiment of a force concentrator 180 operably mounted on one of the pressure sensors 24 of FIG. 5. FIG. 12 is a sectional view taken along lines 12-12 in FIG. 11. As illustrated in FIGS. 11 and 12, each of the force concentrators 180 is positioned between the insole 110 and the sensor board 116, over one of the pressure sensors 24, such that the force concentrators 180 concentrate the user's weight onto the pressure sensor 24 for more accurate readings.

In the embodiment of FIGS. 11 and 12, the force concentrator 180 is a puck-shaped resilient material (e.g., rubber). For purposes of this application, the term puck-shaped is defined to include generally cylindrical constructions as shown, and also equivalent constructions (i.e., a shape that has a similar thickness, but not necessarily a round cross-section). In alternative embodiments, the force concentrator 180 may have another shape, according to the design skills of one skilled in the art. When the user steps on his or her foot, the force compresses the insole 110 and the sensor board 116 against each other. The thickness of the force concentrator 180 directs a larger part of the force directly against the pressure sensor 24. Diligent experimentation has shown that this configuration provides superior results to sensor arrangements that lack such a force concentrator 180.

FIG. 13 is a sectional view of another embodiment of the force concentrator, wherein the force concentrator is formed by a resilient spring element 182 extending opposite the pressure sensor 24, such that the resilient spring element 182 abuts the pressure sensor 24 and directs compressive forced exerted by the user's foot onto the pressure sensor 24, but is resilient enough to prevent damage to the pressure sensor 24 when great force is applied.

FIG. 14A is a sectional view of third embodiment of the force concentrator, wherein the force concentrator is a fluid bladder 184 (e.g., full of air, liquid, gel, or other suitable fluid). In this embodiment, the fluid bladder 184 functions to transmit pressure into the pressure sensor 24, while cushioning the sensor 24 from excessive forces that might damage the sensor 24. Those skilled in the art may devise alternative force concentrators, and such alternatives should be considered within the scope of the present invention.

FIG. 14B is a sectional view of fourth embodiment of the force concentrator, wherein the force concentrator includes an alternative embodiment of the bladder 184. In this embodiment, the bladder 184 includes a fluid connector 185 operably connected to a MEMS pressure sensor 24 that measures the pressure of the fluid from the bladder 184. The pressure sensor 24 may be any form of sensor, transducer, strain gauge, and/or any other form of sensor known in the art.

Figure 15:
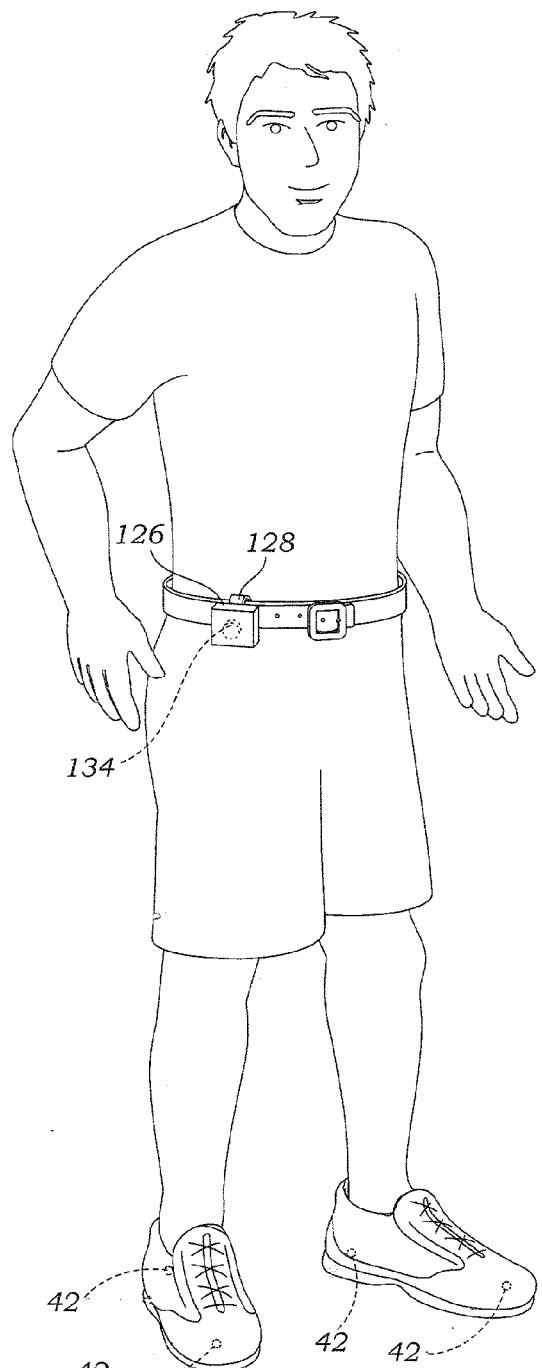
FIG. 15 is a perspective view of a user wearing shoes that incorporate the sensor devices and a belt-mounted reporting device, illustrating how the sensor system may be used to measure body movements from three reference points on the user's body.

FIG. 15 is a perspective view of a user wearing shoes that incorporate the sensor devices 100, and also wearing a belt-mounted reporting device 126. The sensor devices 100 of this embodiment include the accelerometers 42, as discussed above. The belt-mounted reporting device 126 of this embodiment also includes a reporting device accelerometer 134. In this embodiment, the sensor device 100 may be used to measure body movements from three reference points on the user's body, thereby enabling the measurement of movements that cannot be measured using shoe mounted sensors alone.

Figure 16:
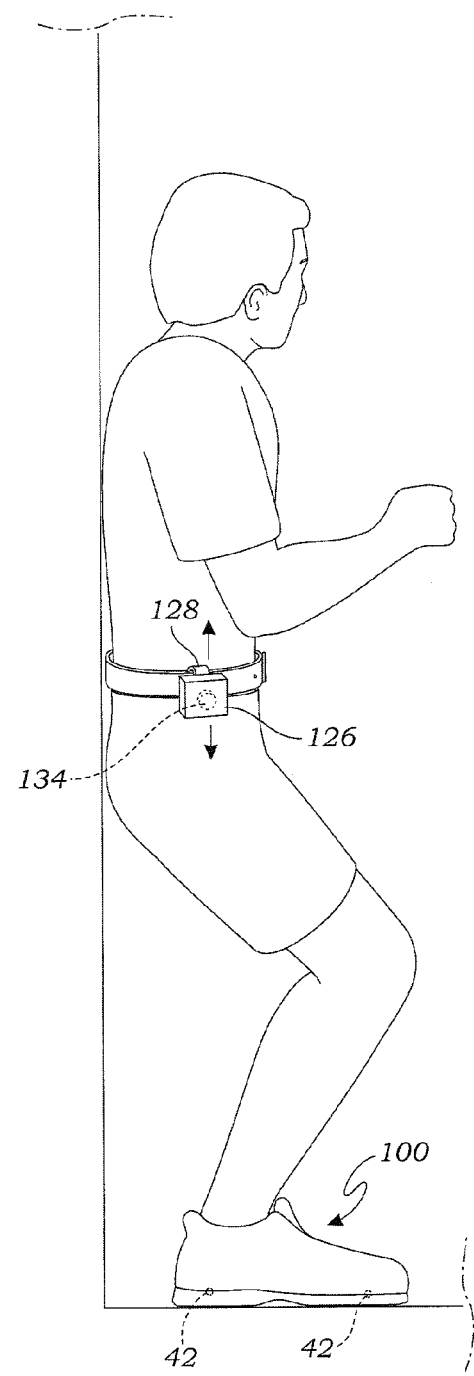
FIG. 16 is a side elevational view of the user of FIG. 15 performing a wall slide exercise that is measured and recorded by the sensor system.

FIG. 16 is a side elevational view of the user of FIG. 15 performing a wall slide exercise that is measured and recorded by the sensor device 100. This is one example of such an exercise that could not ordinarily be measured using system that only tracked the movement of the user's feet, because the user's feet never move in this type of exercise. While the user's feet remain stationary through the exercise, the user's body slides up and down a wall, and this movement is captured by the reporting device accelerometer 134 in the belt-mounted reporting device 126, so that the sensor system can make sure that the exercise is being performed properly, and through the prescribed range of motion. The reporting device 126 may utilize the reporting device alert mechanism 66 (illustrated in FIG. 2) to report when the user has correctly performed the exercise and reached the correct position, and/or report if the user exceeds the correct range of motion (or, alternatively, has failed to go far enough in the exercise. The alert mechanism 66 may utilize the same mechanisms and alerts described in greater detail above, only for the purposes of reporting range of motion, tracked by the accelerometers 42, that than pressure as reported by the pressure sensors. Since many options are discussed above, this is not discussed in greater detail, but the above discussion is incorporated by reference.

Figure 17:
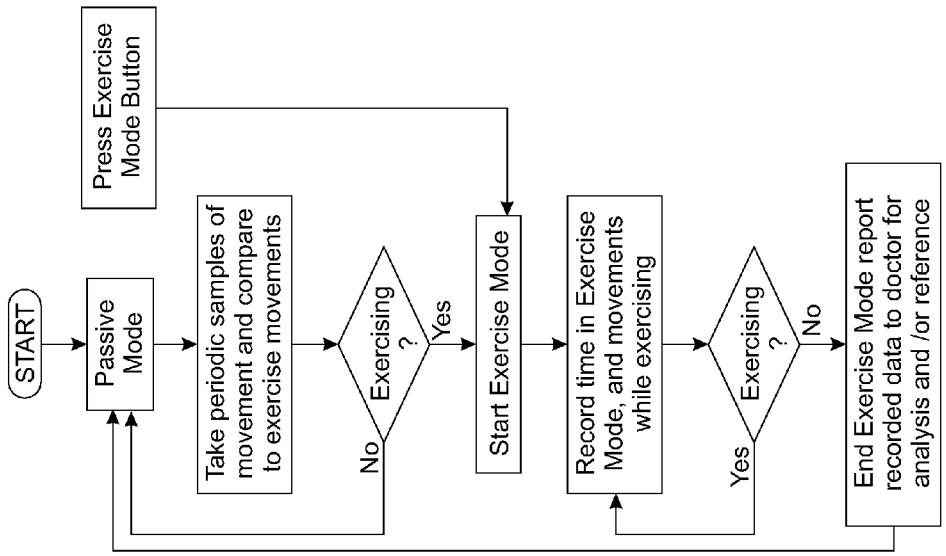
FIG. 17 is a flow diagram illustrating the operation of the sensor system to enter an exercise mode for recording the exercises performed by the user, to help guide rehabilitation of an injury.

FIG. 17 is a flow diagram illustrating the operation of the sensor system to enter an exercise mode for recording the exercises performed by the user, to help guide rehabilitation of an injury. As illustrated in FIG. 17, under normal circumstances, the user may manually switch the reporting device 126 to an exercise mode, wherein the reporting device 126 gathers detailed information about pressures sensed and/or movement of the user. The reporting device 126 may include the button 130 illustrated in FIG. 5, or it may include an alternative means of turning the device 126 to the exercise mode. The data may then be reported to the computer 70 (illustrated in FIG. 2) for review by doctors, physical therapists, and/or the user.

The use of an "exercise mode" is helpful to remind users to do their exercises, and motivates them to do them correctly. People always perform better when they are being monitored, and this mode activation motivates the user to do his or her best.

Not only does the use of the exercise mode help encourage the user to perform the prescribed exercises, it also helps ensure that they are performed correctly, and through the required range of motion (without exceeding the correct range of motion). This can be important because correctly performing the exercises can be difficult. Furthermore, the performance of the exercises will often vary from week to week, so even if the user performs the exercises correctly in a first week, he may need guidance to make sure that he or she correctly changes with time (e.g., increasing the pressure placed on the leg, increasing the range of motion, etc.).

Since the user may forget to switch the sensor system to exercise mode before performing the exercises, the sensor system may include software for monitoring the user's movement to determine if the user has started performing the exercises. The reporting device 126 takes periodic samples of the user's movements to determine if he or she is performing the exercises. If the user is performing the exercises, the reporting device 126 automatically goes into the exercise mode; if the user is not performing the exercises, it remains in passive mode (periodically sampling movement).

Once in exercise mode, the reporting device actively records and stores data from the various sensors described above.

Figure 18:
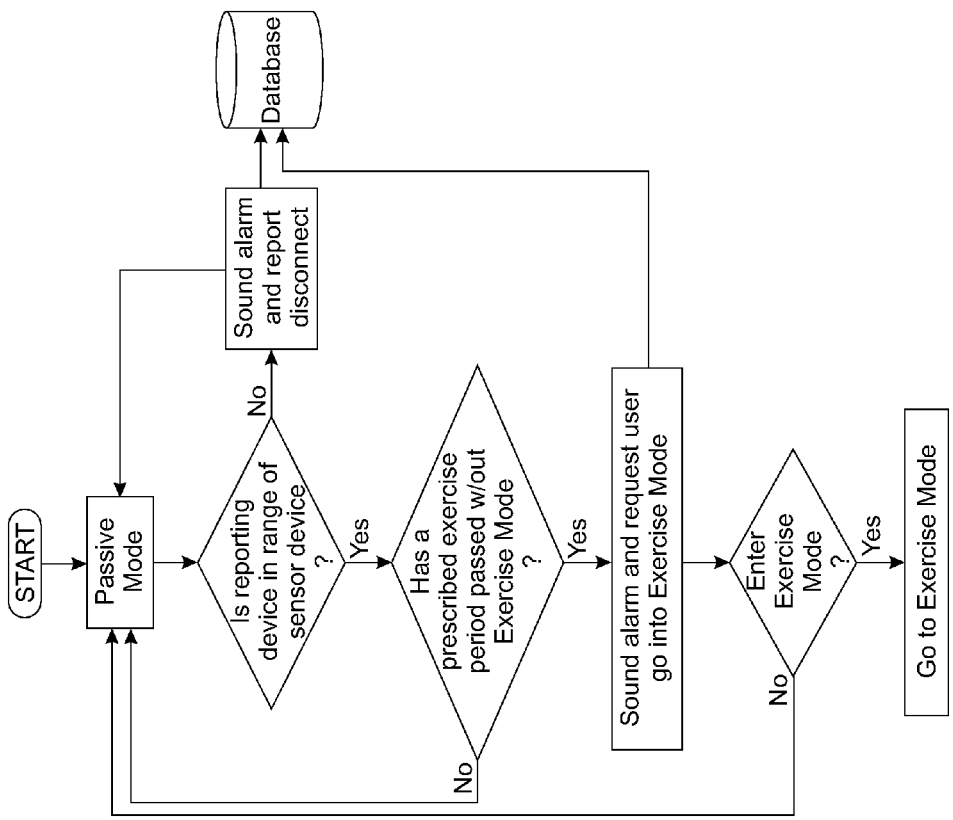
FIG. 18 is a flow diagram illustrating further operations of the sensor system for alerting the user if the reporting device is moved beyond the range of the sensor device, and to also alert the user if he or she forgets to go into exercise mode during the prescribed time periods.

FIG. 18 is a flow diagram illustrating further operations of the sensor system for alerting the user if the reporting device 126 (illustrated in FIG. 5) is moved beyond the range of the sensor device 100 and to also alert the user if he or she forgets to go into exercise mode during the prescribed time periods.

As illustrated in FIG. 18, the sensor system periodically checks to see if the reporting device 126 is within range of the sensor device 100. If the user moves out of range of the reporting device 126, the alert mechanism (element 66 in FIG. 2) is activated so that the user can retrieve the reporting device 126. This can be particularly important if the reporting device 126 is part of a monitoring system designed to avoid fraud, such as monitoring an injury covered by Worker's Compensation.

Since the user may periodically forget his or her exercises, the present sensor system includes software for automatically tracking the entry into and exit from the exercise mode, and alerting the user if an exercise period passes without the user entering exercise mode. The user can then enter exercise mode and perform the required exercises. All of the alarms and other activity may be saved, either in the reporting device memory or in a central database, for reference by the doctor or other treating professional. If the user collecting Worker's Compensation routinely abandons the reporting device, avoiding data collection, he or she may be more closely scrutinized. If the user routinely misses his or her exercises, the doctor or other professional may want to follow up with corrective action.

The data gathered from the various sensors may be collected and displayed using suitable software for the purposes of monitoring patient compliance with rehabilitation regimes, and also for alerting doctors to various problems with the patient using the system.

Figure 19:
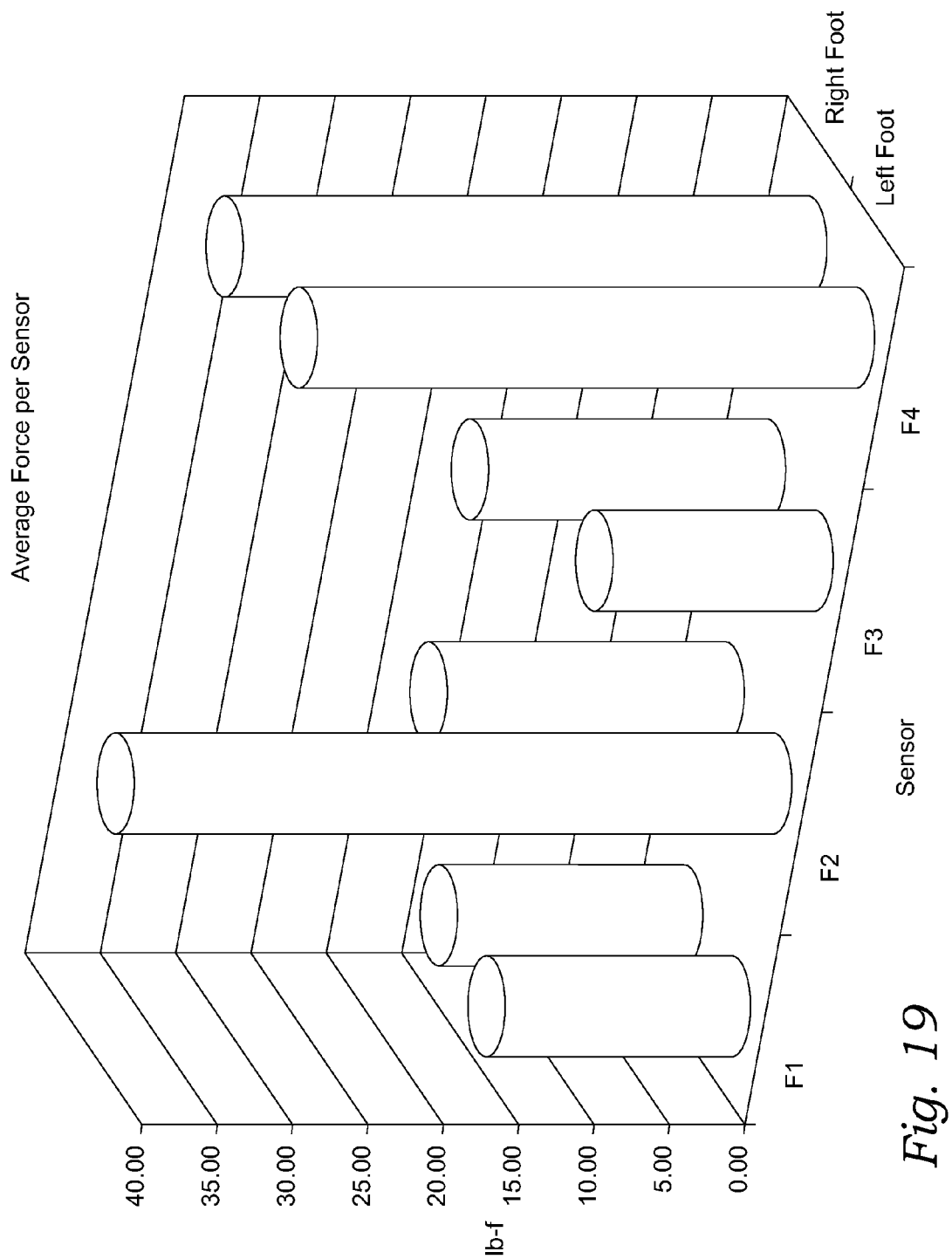
FIG. 19 is a bar graph illustrating pressure data from the four sensors on each of two shoes while the user is standing still.

FIG. 19 is a bar graph illustrating pressure data from the four pressure sensors on each of two shoes while the user is standing still. As illustrated in FIG. 19, the pressure data is collected and averaged to show the quadrants (illustrated in FIG. 10) that are bearing the user's weight. Not only can the pressure data be compared from one foot to another (i.e., the healthy leg compared to the injured leg), the pressure data can also be compared to determine which portion of the user's foot is bearing the weight.

Figure 20:
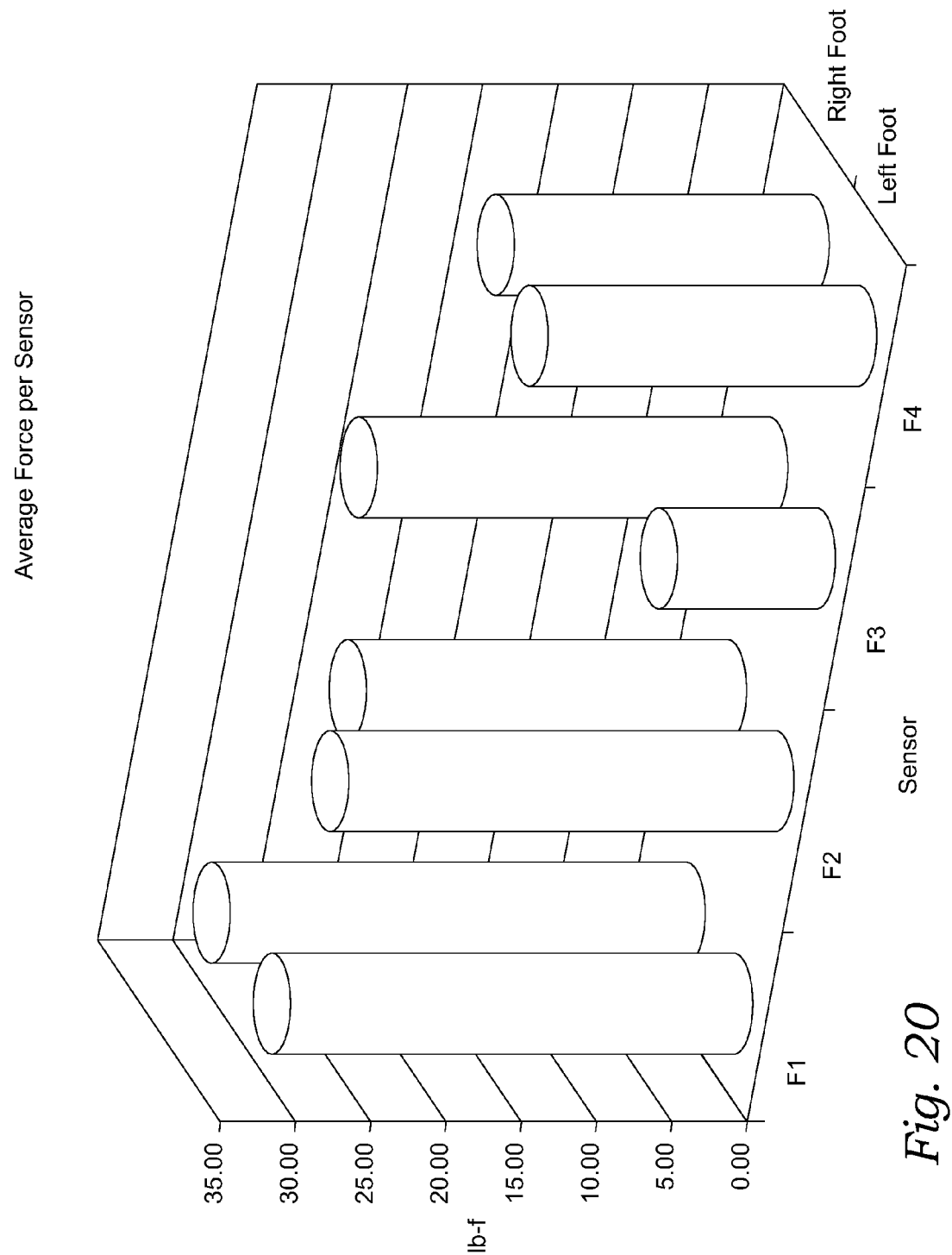
FIG. 20 is a bar graph illustrating pressure data from the four sensors on each of the two shoes while the user is walking.

FIG. 20 is a bar graph illustrating pressure data from the four pressure sensors on each of the two shoes while the user is walking As illustrated in FIG. 20, the pressure data is collected and averaged to show the quadrants (illustrated in FIG. 10) that are bearing the user's weight. Typically there is some correction to make sure that the data collected is correct; for example, the first 2-3 steps and the last 2-3 steps may be disregarded, since the user's stride may change when starting and/or stopping the walk. The averaged data provides insight into the health of the user's legs.

Reduced pressure in a given quadrant, and/or increased pressure in other quadrants, can indicate various physical conditions, injuries, etc. If a given quadrant shows significantly lower pressure, this can indicate that the user is avoiding putting pressure there, perhaps in response to pain, weakness, or as a result of an injury or other condition.

Figure 21:
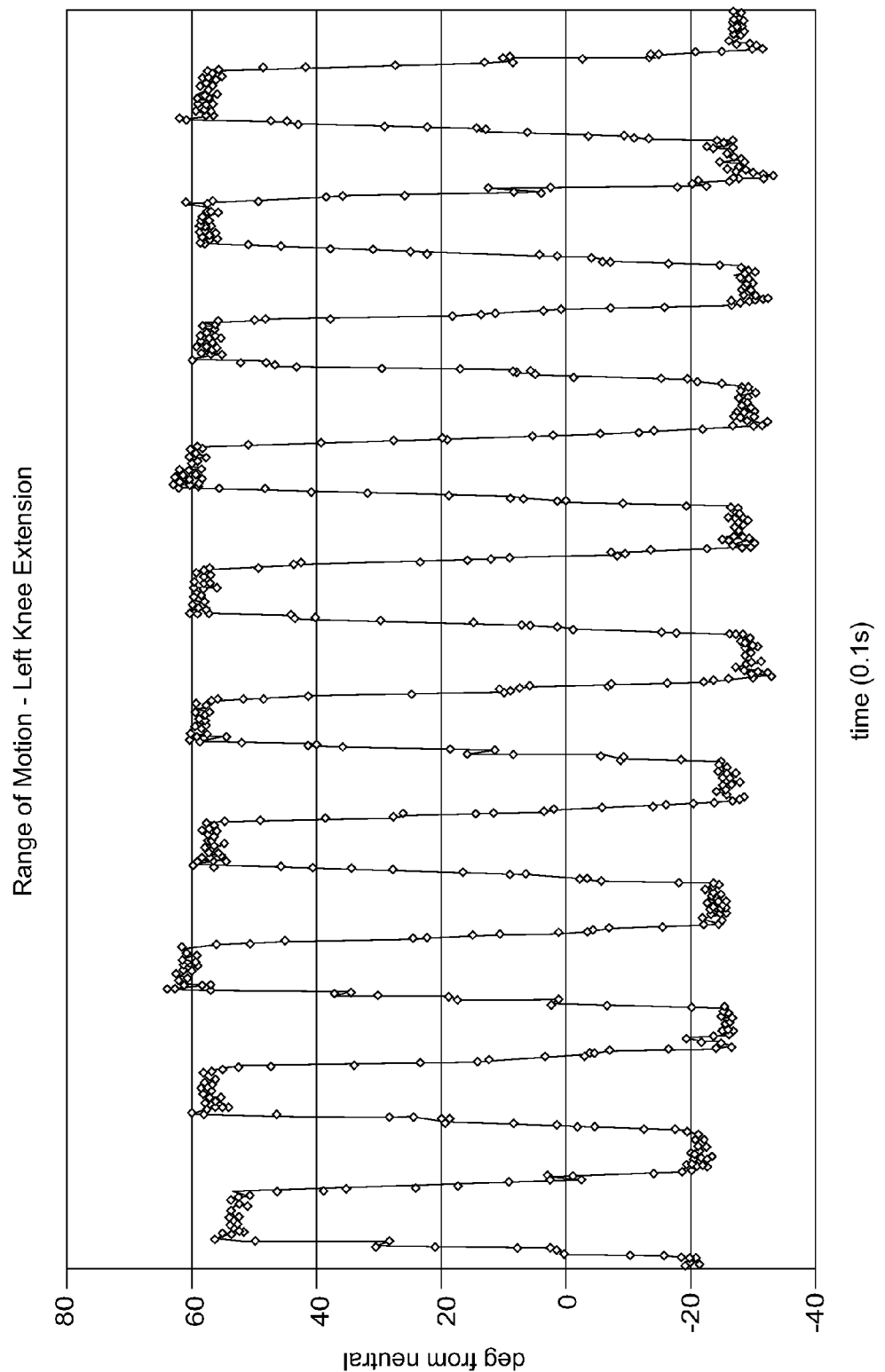
FIG. 21 is a graph of the movement of the two sensor devices in the two shoes during physical rehabilitation exercises, showing movement of the user's legs during the exercises.

FIG. 21 is a graph of the movement of the two sensor devices during physical rehabilitation exercises as measured by the accelerometers, showing movement of the user's legs during the exercises. As with FIGS. 19-20, the movement of the user's legs can indicate injury, weakness, and can enable the physician to track the user's rehabilitation. Following an injury, the user will usually experience a loss in range of motion due to the injury. The range of motion of the injured leg may be compared with the range of motion of the healthy leg, to determine the extent of the loss of range of motion. As rehabilitation progresses, the healthy range of motion should be regained, and this progress can be tracked using the invented system described herein.

The terminology used in the specification provided above is hereby defined to include similar and/or equivalent terms, and/or alternative embodiments that would be considered obvious to one skilled in the art given the teachings of the present patent application. Additionally, the words "a," "an," and "one" are defined to include one or more of the referenced item unless specifically stated otherwise. Also, the terms "have," "include," "contain," and similar terms are defined to mean "comprising" unless specifically stated otherwise.

While the invention has been described with reference to at least one embodiment, it is to be clearly understood by those skilled in the art that the invention is not limited thereto. Rather, the scope of the invention is to be interpreted only in conjunction with the appended claims.

What is claimed is:

1. A sensor device comprising:
an insole having a sensor body abutting the insole;
pressure sensors operably mounted on the sensor body for sensing pressure exerted on the insole, the pressure sensors functioning to generate a pressure data signal indicating the pressures sensed;
an accelerometer mounted on the insole, the accelerometer functioning to generate a movement data signal indicating the measuring movement of the insole;
a transmitter for transmitting the pressure data signal and the movement data signal;
and a reporting device having a receiver for receiving the pressure data signal and the movement data signal, the reporting device further having a processor and a computer-readable medium for storing the pressure data signal and the movement data signal;
wherein the sensor body includes a pair of sensor boards, a front sensor board and a rear sensor board, that each include two of the pressure sensors, wherein each of the pressure sensors is arranged in one of four quadrants formed by a longitudinal center of gravity and a lateral center of gravity, the longitudinal center of gravity being formed along the long axis of the foot at the center of balance when the user is standing stationary, and the lateral center of gravity being formed perpendicular to the longitudinal center of gravity at the user's center of gravity when standing stationary.

2. The sensor device of claim 1, wherein each pressure sensor is mounted on the sensor body such that it is abuts the insole.

3. The sensor device of claim 2, wherein the sensor body includes at least one flexible printed circuit board.

4. The sensor device of claim 1, further comprising a force concentrator mounted over each of the pressure sensors, between the sensor body and the insole, such that compressive forces between the sensor body and the insole are concentrated on the pressure sensor.

5. The sensor device of claim 4, wherein each of the force concentrators comprises a puck-shaped element shaped to fit over one of the pressure sensors.

6. The sensor device of claim 5, wherein each of the force concentrators is resilient.

7. The sensor device of claim 4, wherein each of the force concentrators comprises a spring element shaped to fit over one of the pressure sensors.

8. The sensor device of claim 4, wherein each of the force concentrators comprises a bladder element shaped to fit over one of the pressure sensors.

9. The sensor device of claim 1, wherein the insole includes a front recess and a rear recess, wherein the sensor board includes two sensor boards, and wherein one of the sensor boards is positioned in the front recess of the insole and the other is positioned in the rear recess.

10. The sensor device of claim 1, wherein the insole includes a flexible slipper upper so that the insole may be worn on a user's foot.

11. The sensor device of claim 1, wherein the reporting device includes a reporting device accelerometer.

12. A sensor device comprising:

an insole having a sensor body abutting the insole;

pressure sensors operably mounted on the sensor body for sensing pressure from the user, the pressure sensors functioning to generate a pressure data signal indicating the pressures sensed;

a force concentrator mounted over each of the pressure sensors and between the sensor body and the insole, such that compressive forces between the sensor body and the insole are concentrated on the pressure sensor;

an accelerometer mounted on the insole, the accelerometer functioning to generate a movement data signal indicating the measuring movement of the insole;

a transmitter for transmitting the pressure data signal and the movement data signal;

and a reporting device having a receiver for receiving the pressure data signal and the movement data signal, the reporting device further having a processor and a computer-readable medium for storing the pressure data signal and the movement data signal;

wherein the sensor body includes a pair of sensor boards, a front sensor board and a rear sensor board, that each include two of the pressure sensors, wherein each of the pressure sensors is arranged in one of four quadrants formed by a longitudinal center of gravity and a lateral center of gravity, the longitudinal center of gravity being formed along the long axis of the foot at the center of balance when the user is standing stationary, and the lateral center of gravity being formed perpendicular to the longitudinal center of gravity at the user's center of gravity when standing stationary.

13. The sensor device of claim 12, wherein each of the force concentrators comprises a puck-shaped element shaped to fit over one of the pressure sensors.

14. The sensor device of claim 12, wherein each of the force concentrators comprises a spring element shaped to fit over one of the pressure sensors.

15. The sensor device of claim 12, wherein each of the force concentrators comprises a bladder element shaped to fit over one of the pressure sensors.

16. The sensor device of claim 12, wherein the insole includes a front recess and a rear recess, wherein the sensor board includes two sensor boards, and wherein one of the sensor boards is positioned in the front recess of the insole and the other is positioned in the rear recess.

17. The sensor device of claim 12, wherein the insole includes a flexible slipper upper.

18. The sensor device of claim 12, wherein the reporting device includes a reporting device accelerometer.

* * * * *